United States Patent [19]

Gustafson et al.

[11] Patent Number: 4,886,761

[45] Date of Patent: Dec. 12, 1989

[54] POLYSILICON BINDING ASSAY SUPPORT AND METHODS

[75] Inventors: Eric K. Gustafson, Palo Alto; Rick Trebino, Livermore; John Lee, Cupertino, all of Calif.

[73] Assignee: Yellowstone Diagnostics Corporation, Sunnyvale, Calif.

[21] Appl. No.: 30,327

[22] Filed: Mar. 26, 1987

[51] Int. Cl.[4] .................. G01N 33/543; G01N 33/566; G01N 21/00; G01N 21/06

[52] U.S. Cl. ..................................... 436/518; 436/501; 436/524; 436/810; 422/55; 422/57; 422/58

[58] Field of Search ............... 436/518, 524, 527, 810; 422/55, 57, 58

[56] References Cited

U.S. PATENT DOCUMENTS

| | | | |
|---|---|---|---|
| 4,299,916 | 11/1981 | Litman et al. | 435/6 |
| 4,334,880 | 6/1982 | Malmros | 436/501 |
| 4,525,452 | 6/1985 | Jones et al. | 435/7 |
| 4,554,088 | 11/1985 | Whitehead et al. | 436/527 |

Primary Examiner—Robert J. Warden
Assistant Examiner—Janelle Graeter
Attorney, Agent, or Firm—William B. Walker

[57] ABSTRACT

An improved binding assay plate having greatly reduced non-specific binding with proteinaceous reagents comprising a polysilicon surface having a binding reagent adhered thereto, the surface having a coating adsorbed thereon of a proteinaceous non-specific binding inhibitor. This binding assay product is prepared by adhering binding reagent to a polysilicon surface and then treating the surface with the proteinaceous non-specific binding inhibitor.

The binding assay method comprises the steps of contacting the polysilicon surface having a primary binding reagent and non-specific binding inhibitor adhered to the surface thereof with a solution containing an analyte with which the primary binding reagent specifically binds for a time sufficient to permit conjugation of analyte with the primary binding reagent and determining the analyte bound to the polysilicon surface. The plate is suitable for both sandwich and competition immunoassays. The reduction of non-specific binding produces a substantial increase in sensitivity.

15 Claims, 1 Drawing Sheet

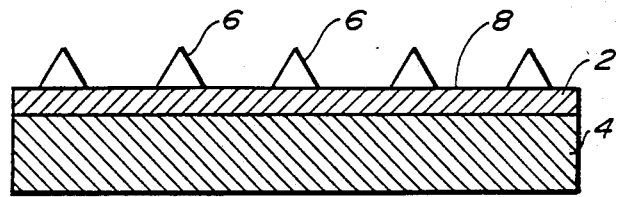
FIG._1.
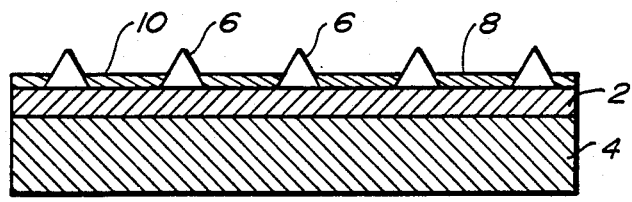
FIG._2.
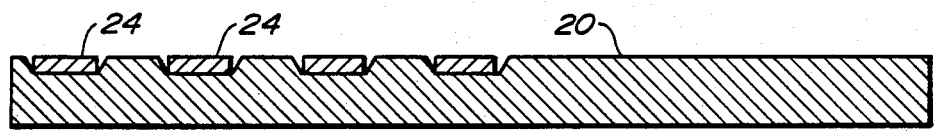
FIG._3.

POLYSILICON BINDING ASSAY SUPPORT AND METHODS

FIELD OF THE INVENTION

This invention relates to heterogeneous binding assays using an improved insoluble support and reagents and materials therefor. In particular, this invention relates to novel combinations of polysilicon supports and binding assay reagents having greatly reduced non-specific binding characteristics and methods for using them.

BACKGROUND OF THE INVENTION

A variety of methods have been developed for determining substances capable of being bound specifically, generally immunochemical substances, including antigens, antibodies, haptens and other low molecular weight substances. In one approach, binding reagents capable of binding with a target analyte are bound to an insoluble support. When the support is contacted with the sample containing the analyte, the analyte is bound to the binding reagent, and is removed from the sample when the insoluble support is separated from the sample. Methods using insolubilizing supports include radioimmunoassay techniques, fluoroimmunoassays, enzyme immunoassays, transistor bridge probes, indium reflective surface methods, ultrasonic probes, and the like.

This approach is particularly useful in sandwich and competition immunoassays, wherein the insoluble support bearing the binding reagent conjugated with the analyte is further reacted or conjugated with labeled reagents which bind specifically with the analyte or unconjugated binding reagent. Measurement of the label bound to the insoluble support can be correlated with the amount of analyte in the sample. Binding of the labeled reagent exclusively with the analyte is intended in these procedures. However, a certain proportion of the labeled reagent inevitably binds directly with the insoluble support in a non-specific binding process. This "non-specific" binding introduces an error variable which contributes a background signal limiting the sensitivity of the assay method. This type of limit has become increasingly important with the introduction of labels yielding a high signal over the environmental background and the development of assays for low trace quantities of analytes.

As a partial solution to the problem of non-specific binding, an insoluble support to which a binding reagent has been bonded is sometimes treated with a solution containing a non-immune protein or amino acid polymer which coats the support surface, presenting a barrier to further protein binding by physical adsorption. This non-specific binding inhibitor reduces the non-specific binding, but with the insoluble supports previously used in heterogeneous sandwich and competition immunoassays, a substantial level of non-specific binding remained.

This invention is based on the discovery that polysilicon surfaces are substantially superior to surfaces previously used for sandwich and competition immunoassays because the non-specific binding of secondary reagents to the surface can be almost entirely inhibited with a coating of a suitable protein.

A wide variety of insoluble materials have been used or suggested for use as insoluble supports. Organic and inorganic polymers, both natural and synthetic, have been used. Examples of such polymers include polyethylene, polypropylene, polybutylene, poly(4-methylbutylene), butyl rubber, silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which have been used as insoluble supports are latices of the above polymers, silica gel, glass, paper, insoluble protein, metals, metalloids, metal oxides, magnetic materials, cermets and the like.

DESCRIPTION OF THE PRIOR ART

Metal surfaces have been previously used in immunological procedures. A reflectance method for quantification of immunological reactions on polished crystalline silicon wafer surfaces has been described by Arwin, H. et al, *Analytical Biochemistry.* 154:106–112 (1985). Indium surface reflection methods are described by Giaever in U.S. Pat. Nos. 3,853,467, 3,926,564, 3,960,488, 3,960,489, 3,960,490, 3,975,238, 3,979,184, 3,979,509, 4,011,308, 4,018,886, 4,054,646, 4,115,535, 4,172,827 and 4,181,501. Liquid layer thicknesses can be monitored by a reflectance method described in U.S. Pat. No. 3,960,451. These relatively insensitive methods are not suitable for detecting analytes in the low concentrations at which non-specific binding presents a limitation to sensitivity, and no problems relating to non-specific binding have been reported.

Biosensors and their use in assays are described by Pace, S., *Medical Instrumentation.* 19(4):168–172 (1985). A variety of semiconductor materials including polysilicon have been tried as antibody supports in these devices, because of their semiconductor characteristics. However, non-specific binding problems have not been reported with these devices, perhaps because other more significant obstacles to sensitivity remain unsolved. In any event, neither the problems of non-specific binding or any solution thereof has been described in the literature for biosensors. Pace et al do not suggest the use of polysilicon outside of the biosensor context and do not report any non-specific binding problems or solutions.

SUMMARY OF THE INVENTION

The binding assay product of this invention is a polysilicon binding assay surface having a binding reagent adhered thereto, wherein the polysilicon surface is not a part of a semiconductor device. The binding reagent can be an antibody, antigen, hapten, protein A, lectin, biotin, avidin, DNA or RNA probes, DNA or RNA probe-protein conjugates, other nucleotides, an enzyme or enzyme substrate, or the like. Preferably, the polysilicon binding assay surface has a non-specific binding inhibitor such as a water-soluble non-immune protein or polyamino acid adsorbed to the surface thereof. The polysilicon binding assay surface can be mounted on a solid device such as a microwell or dipstick, preferably made of a non-specific binding composition. In one embodiment, the polysilicon can be a thin layer supported on a smooth surface of silicon dioxide.

The binding assay method of this invention includes the steps of (a) contacting the polysilicon binding assay surface described above with a sample solution containing an analyte which is specifically bound by the binding reagent for a time sufficient to permit conjugation between the binding reagent and the analyte;
(b) removing residual sample solution from the polysilicon surface; and
(c) determining the analyte bound to the polysilicon surface.

When the binding agent is a primary binding reagent, the analyte bound to the polysilicon surface can be determined in Step (c) by contacting the polysilicon surface with a reagent solution of a labeled secondary binding reagent which binds specifically with the analyte for a time sufficient for analyte conjugation with the secondary binding reagent to occur, removing residual reagent solution, and determining the label bound to the polysilicon surface. Suitable labels include an enzyme, chromophore, fluorophore, or radioactive compound. If the label is an enzyme, it can be determined by contacting the insoluble support with a substrate which in the presence of the enzyme, produces a detectable chromophore or fluorophore, and determining the chromophore or fluorophore produced thereby. Suitable enzymes include horseradish peroxidase, $\beta$-galactosidase and alkaline phosphatase.

In a competition binding assay according to this invention, the binding reagent bound to the insoluble surface and the analyte have the same binding epitopes, and the polysilicon surface is contacted with a solution containing analyte and a labeled secondary binding reagent for a time sufficient to permit conjugation of primary and secondary binding reagents, and determining the presence and/or amount of label remaining bound to the polysilicon surface.

BRIEF DESCRIPTION OF THE DRAWINGS

FIG. 1 is a schematic cross-sectional representation of a polysilicon coated substrate having a binding reagent adhering to the surface thereof.

FIG. 2 is a schematic cross-sectional representation of the polysilicon coated substrate of FIG. 1 with a coating of non-specific binding inhibitor on the surface thereof.

FIG. 3 is a cross-sectional view of a dipstick plate having polysilicon chips with a primary binding reagent, mounted on the surface thereof.

DETAILED DESCRIPTION OF THE INVENTION

The binding assay product of this invention is a polysilicon surface having a binding reagent adhered thereto, the surface having a coating adsorbed thereon of a proteinaceous non-specific binding inhibitor. This binding assay product is prepared by adhering binding reagent to a polysilicon surface and then treating the surface with the proteinaceous non-specific binding inhibitor.

The term "binding reagent" is used herein to designate one member of any binding pair of compounds or materials which selectively bind to form a conjugate. The binding reagent can be a member of the well-known antibody-antigen or antibody-hapten pairs wherein the antibody binds selectively with the respective antigen or hapten. The binding reagent can also be a member of other types of binding pairs such as biotin-avidin; lectin-sugar; IgG antibody Fc portion with protein A; enzyme-enzyme substrate; DNA or RNA binding with DNA, DNA fragments or other nucleotide sequences; and the like. In general, the binding reagent is selected to bind specifically or selectively with the analyte, the material for which a sample is assayed.

The term "binding assay", is used herein to designate an assay using any binding reaction between a binding reagent and the other member of the binding pair which is selectively bindable therewith.

The polysilicon surface is preferably a thin film of polysilicon deposited on a suitable surface, preferably a highly polished surface such as a single crystalline silicon wafer or a silicon dioxide surface. Polysilicon films were developed in the semiconductor industry as valuable dielectric materials. They are used as gate electrodes in MOS devices, for high value resistors, diffusion sources to form shallow junctions, conductors and to ensure ohmic contact to crystalline silicon. The term "polysilicon" as used herein is synonymous with the term "polycrystalline silicon". These films are conventionally prepared by chemical vapor deposition techniques. These films and method for their preparation are described by A. C. Adams in "Dielectric and Polysilicon Film Deposition", VLSI TECHNOLOGY. (S.M.Sze ed.) New York: McGraw-Hill, pp 93–129 (1983) and the citations therein, the entire contents of which are hereby incorporated by reference. The surface upon which the polysilicon is coated can be any material which is stable at polysilicon deposition temperatures. It can be prepared by pyrolyzing silane at 600° to 650° C. in a partial vacuum. Lower pyrolysis temperatures are suitable with more reactive silicon sources such as disilane.

Primary binding reagent is adhered to the insoluble support. For many applications, the primary binding reagent is chosen to bind selectively with an analyte to be determined or measured in a sample.

The primary binding reagent can be bound to the insoluble support by adsorption, ionic bonding, van der Waals adsorption, electrostatic bonding, or other non-covalent bonding, or it can be bound to the insoluble support by covalent bonding. Procedures for non-covalent bonding are described in U.S. Pat. No. 4,528,267. Procedures for covalently bonding antibodies and antigens to insoluble supports are described by Ichiro Chibata in IMMOBILIZED ENZYMES. Halsted Press: New York (1978) and A. Cuatrecasas, *J. Bio. Chem.* 245:3059 (1970), the entire contents of which are hereby incorporated by reference. The surface can be coated with a protein and coupled with the primary binding reagent using procedures described in U.S. Pat. No. 4,210,418 using glutaraldehyde as a coupling agent, for example. In a still further procedure, the surface can be coated with a layer having free isocyanate groups such as a polyether isocyanate, and application of the antibody or antigen in aqueous solution thereto effects the requisite bonding.

When the binding reagent is a proteinaceous material, it is preferably bound to the polysilicon surface by physical adsorption. We have discovered that proteins form a strong adsorption bond with polysilicon surfaces.

If the binding reagent is a non-proteinaceous material or a hapten, it can be bonded or conjugated with a proteinaceous material or similar water-soluble polymer for physical adsorption with the polysilicon surface. Suitable water soluble polymers include bovine serum albumins (BSA), human (HSA), rabbit (RSA), goat (GSA), sheep (SHA), horse (HOSA), etc.; serum gamma globulin, of the previously described animals and other animal proteins such as ovalbumin, fibrinogen, thrombin, transferin, glycoproteins, etc. Suitable water-soluble amino acid polymers include polylysine, polyglutamic acid, polyalanine, polyhistidine, polymethionine, polyproline, etc. The hapten can be covalently bonded to the water-soluble protein or amino acid polymer with conventional coupling agents using methods which are well known in the art and are not a part of this invention.

FIG. 1 is a schematic cross-sectional representation of a polysilicon coated substrate having a primary binding reagent adhering to the surface thereof. The polysilicon film 2 is supported by the substrate 4. Primary binding reagent 6 is bonded to the surface 8 of the film 2, for example by physical adsorption. Portions of the surface 8 remain exposed, available for uncontrolled non-specific binding with proteinaceous reagents in the binding assay.

The primary binding reagent is preferably physically adsorbed onto the polysilicon surface. In one suitable procedure for adsorbence bonding primary binding reagent to the surface of an insoluble support, a primary binding reagent such as an antibody, antigen or hapten-protein protein conjugate is applied to the polysilicon surface in an aqueous buffer solution. The surface can be initially cleaned with a cleaning fluid such as methanol and dried. The buffered primary binding reagent solution is placed in a container with the support bearing the polysilicon surface and incubated at room temperature until adsorption occurs, for example for from 2 to 18 hours and preferable from 16 to 18 hours, at temperatures of from 4° to 40° C. and preferable from 20° to 26° C. The surface is then rinsed with a buffered saline solution and dried.

The concentration of primary binding reagent in the buffer solution is selected to provide the desired reagent density on the polysilicon surface. The primary binding reagent solution can contain from 0.02 to 100 micrograms/ml of the primary binding reagent and preferably contains from 10 to 100 micrograms/ml of the primary binding reagent in a buffered solution having a pH of from 6.5 to 9.0 and preferably from 7.4 to 8.5.

The primary binding reagents are selected to selectively bind with the analyte to be measured in a sample. For example, the primary binding reagent can be a polyclonal antibody, a monoclonal antibody or a mixture of monoclonal antibodies binding specifically with a sample analyte to be measured. For determining antibodies binding with a specific antigen in a sample, the binding reagent can be an antigen binding with the analyte antibody, such as Streptococcus A antigen which binds with Streptococcus A in a liquid sample. The primary binding reagent can also be a hapten or antigen conjugate with a water-soluble protein or polymer which adheres more strongly or more uniformly to the polysilicon surface than the simple hapten or antigen. The primary binding reagent can be other binding reagents such as biotin for the analyte avidin, avidin for the analyte biotin, lectin, Protein A for antibodies binding therewith, a DNA or RNA probe, an enzyme, an enzyme substrate, and the like.

The surface 8 is then rinsed and dried. A suitable rinse solution is an aqueous phosphate buffer solution such as is described in U.S.Pat. No. 4,528,267 having a phosphate molarity of from 0.0001 to 0.05, a pH of from 6 to 8 and containing from 0.001 to 0.1 weight percent non-ionic surfactant and from 0.0001 to 0.5 weight percent of a suitable water-soluble polymer such as an animal serum albumin, and from 0.5 to 1.0 weight percent of a sugar. Suitable non-ionic surfactants include polyoxyethylene ethers (BRIJ) such as lauryl, cetyl, oleyl, stearyl, and tridecyl polyoxyethylene ethers; polyoxyethylenesorbitans (TWEEN) such as polyoxyethylenesorbitan monolaurate, monopalmitate, monostearate, monoleate and trioleates; and other polyoxyethylene ethers (TRITON), for example. A preferred nonionic surfactant is octylphenoxypolyethoxy ethanol having 40 ethylene oxide units (TRITON X-405, Rohm and Haas Company). Suitable water-soluble polymers include include bovine serum albumins (BSA), human (HSA), rabbit (RSA), goat (GSA), sheep (SHA), horse (HOSA), etc.; serum gamma globulin, of the previously described animals and other animal proteins such as ovalbumin, fibrinogen, thrombin, transferrin, glycoproteins, etc. Suitable water-soluble amino acid polymers include polylysine, polyglutamic acid, polyalanine, polyhistidine, polymethionine, polyproline, etc. Suitable sugars include sucrose, fructose, maltose and the like.

The composite product is then ready for mounting on a suitable binding assay support such as a microwell surface, dipstick or other insoluble support configured for use in a particular binding assay system. The reference to dipstick in this application is by way of example, not by way of limitation, and it is intended to include application of polysilicon surfaces to all insoluble surfaces within the scope of this invention.

FIG. 3 is a cross-sectional view of a dipstick plate having mounted thereon, polysilicon chips with a primary binding reagent on the surface thereof. If the polysilicon film is on a semiconductor wafer such as a silicon wafer, it is preferably cut into chips, that is, squares or other shapes having the size and surface area desired for a particular application. The chips 24 are then mounted in receptor cavities of the dipstick 20. Non-specific binding inhibitor is applied to the dipstick and the exposed surface of the chips 24.

The materials from which the dipstick surfaces are made should be non-binding to minimize non-specific binding during the binding assay procedure. Suitable dipstick surface materials include polyolefins such as polyethylene and polypropylene, hydrophilic polysilicon and polysiloxane polymers, and polymers which have been treated to render the surface non-binding to proteinaceous materials.

The binding assay method of this invention comprises the steps of contacting the polysilicon surface having a primary binding reagent and preferably with a non-specific binding inhibitor adhered to the surface thereof with a solution containing an analyte with which the primary binding reagent specifically binds for a time sufficient to permit conjugation of analyte with the primary binding reagent and determining the analyte bound to the polysilicon surface.

The incubation time required for conjugation of primary binding reagent and analyte depends upon the temperature and nature of reagents. Suitable incubation times are from 15 to 180 minutes at temperatures within the range of from 18° to 40° C., the preferred contact time for most binding pairs being from 30 to 60 minutes at temperatures of from 20° to 26° C.

The solution containing the analyte is then removed from the surface. Surplus liquid is removed, and the surface is rinsed with a suitable rinse solution such as described hereinabove.

The presence and amount of analyte bound to the polysilicon surface is then determined. In a sandwich binding assay according to this invention, the analyte is preferably determined by contacting the polysilicon surface having analyte conjugated with primary binding reagent thereon with a solution of a labeled secondary binding reagent which specifically binds with the analyte and determining the presence and/or amount of label remaining bound to the polysilicon surface.

The labels can be bonded or coupled to the secondary binding reagents by chemical or physical bonding. Ligands and groups which can be conjugated to the secondary binding reagents include elements, compounds or biological materials which have physical or chemical characteristics which can be used to distinguish the reagents to which they are bonded from compounds and materials in the sample being tested. As a general principle, methods suitable for linking a label with an antibody are equally suitable for linking or bonding the label to other proteinaceous binding reagents. Although the following procedures are described in terms of conjugating labels to antibodies, their use to conjugate labels to other secondary binding reagents are also intended.

The specific activity of a radio-labeled antibody depends upon the half-life, isotopic purity of the radioactive label and how the label is incorporated into the antigen or antibody. Table A lists several commonly used isotopes, their specific activities and half-lives. In binding assay tests, the higher the specific activity, in general, the better the sensitivity.

TABLE A

| Isotope | Specific Activity of pure Isotope | Half-Life (Curies/mole) |
| --- | --- | --- |
| $14_C$ | $6.25 \times 10^1$ | 5720 years |
| $3_H$ | $2.91 \times 10^4$ | 12.5 years |
| $35_S$ | $1.50 \times 10^6$ | 87 days |
| $125_I$ | $2.18 \times 10^6$ | 60 days |
| $32_P$ | $3.16 \times 10^6$ | 14.3 days |
| $131_I$ | $1.62 \times 10^7$ | 8.1 days |

Procedures for labeling proteinaceous binding reagents with radioactive isotopes listed in Table A are generally known in the art. Tritium labeling procedures are described in U.S. Pat. No. 4,302,438, for example. Iodinating, tritium labeling and $35S$ labeling procedures especially adapted for antibodies are described by Goding, J.W. MONOCLONAL ANTIBODIES: PRINCIPLES AND PRACTICE. New York: Academic Press pp 124–126 (1983) and the references cited therein. Other procedures for iodinating antibodies are described by Hunter and Greenwood, Nature. 144:945 (1962) and David et al, Biochemistry. 13:1014–1021 (1974) and in U.S.Pat.Nos. 3,867,517 and 4,376,110.

Procedures for iodinating antibodies are described by Greenwood, F. et al, "The preparation of $131I$-labeled human growth hormone of high specific radioactivity," Biochem.J. 89:114–123 (1963); Marchalonis, J. "An enzymatic method for the trace iodination of immunoglobulins and other proteins," Biochem.J. 113:299–305 (1969); and Morrison, M. et al. "Use of lactoperoxidase catalyzed iodination in immunochemical studies," Immunochemistry. 8:289–297 (1971). Procedures for $99Tc$-labeling are described by Rhodes, B. et al. "$99Tc$-Labeling and acceptance testing of radiolabeled antibodies and antibody fragments," in Burchiel, S. et al (eds.), TUMOR IMAGING: THE RADIOIMMUNOCHEMICAL DETECTION OF CANCER. New York: Masson 111–123 (1982), and the references cited therein. Procedures suitable for 111 In-labeling antibodies are described by Hnatowich, D.J. et al. J.Immul.-Methods. 65:147–157 (1983); Hnatowich, D. J. et al. Science. 220:613–615 (1983) and Buckley, R. G. et al F.E.B.S. 166:202–204 (1984).

Antibodies labeled with enzymes are useful for in vitro diagnostic tests such as are described in U.S. patent application Ser. No. 622,525, now abandoned, filed June 20, 1984. Examples of suitable systems, coupling procedures and substrate reactions therewith are disclosed in U.S. Pat. Nos. Re. 31,006, Bl 3,654,090, 4,214,048, 4,289,747, 4,302,438, 4,312,943, 4,376,110 and the references cited therein, for example. Examples of other suitable systems are described by Pesce et al, Clin.Chem. 20(3):353–359 (1974) and Wisdom, G., Clin.Chem. 22:1243 (1976).

A list of suitable enzyme classes and specific examples for each class follow:

TABLE B

| Class | Enzyme Example |
| --- | --- |
| Hydrolases Carbohydroases | Amylases |
| Nucleases | Polynucleotidase |
| Amidases | Arginase |
| Purine deaminases | Adenase |
| Peptidases | Aminopolypeptidase |
| Proteinases | Pepsin |
| Esterases | Lipases |
| Iron Enzymes | Catalase |
| Copper Enzymes | Tyrosinases |
| Enzymes containing Coenzymes | Alcohol dehydrogenase |
| Enzymes reducing cytochrome | Succinic dehydrogenase |
| Yellow enzymes | Diaphorase |
| Mutases | Glyoxalase |
| Demolases | Aldolase |
| Oxidases | Glucose oxidase |
| | Horse radish peroxidase |
| Phosphatases | Alkaline phosphatase |
| Other enzymes | $\beta$-galactosidase |
| | Phosphorylases |
| | Hexokinases |

A list of suitable enzymes are described in Hawk, et al. PRACTICAL PHYSIOLOGICAL CHEMISTRY, New York: McGraw-Hill pp 306–397 (1954).

Fluorogenic enzymes (enzymes in the presence of which a selected substrate will produce a fluorescent product) are useful labeling moieties. Methods for selectively conjugating enzymes to antibodies without impairing the ability of the antibody to bind with antigen are well known in the art. Suitable enzymes and procedures for coupling them to antibodies are described by Wilson, M. et al. Recent developments in the periodate method for conjugating horseradish peroxidase (HRPO) to antibodies. INTERNATIONAL CONFERENCE IN IMMUNOFLUORESCENCE AND RELATED STAINING TECHNIQUES. W. Knapp et al, editors. Amsterdam: Elsevier pp 215–244 (1978), Sullivan, M. et al. Enzyme immunoassay: a review. Annals of Clinical Biochemistry. 16:221–240 (1979) and in U.S. Pat. No. 4,190,496, for example. The preferred fluorogenic enzymes and suitable substrates corresponding thereto include horseradish peroxidase for which a suitable substrate is homovanillic acid or 4-hydroxy-3-methoxy-phenylacetic acid, $\beta$-galactosidase for which a suitable substrate is 4-methylumbelliferyl-$\beta$-D-galactoside, alkaline phosphatase for which a suitable substrate is 4-methylumbelliferyl phosphate and other umbelliferyl phosphates such as 4-carboxyumbelliferyl phosphate and umbelliferyl phosphate 4-carboxyalkylesters, etc.

Examples of suitable procedures for enzyme labeling the antibody include the use of carbodiimides, dialdehydes, and bifunctional coupling reagents. Linkage of enzymes through amide groups can be achieved by treating the proteins with thionyl chloride, N-hydroxysuccinimide or similar reagents in an anhydrous solvent such as dimethylformamide, dioxane, dimethylsulfoide, tetrahydrofuran, or the like. Alternative coupling agents include carbodiimides such as 1-ethyl-3-(3-N,N'-dimethylaminopropyl)carbodiimide or 1-cyclohexyl-3-(2-morpholinoethyl)carbodiimide methyl-p-toluenesulfonate.

The carbohydrate moiety of an enzyme can also be oxidized to an aldehyde and reacted with lysyl amino groups of immunoglobulins to form a Schiffs base. Reduction with sodium borohydride effects a stable linkage of enzyme and antibody. Horseradish peroxidase with antibody can be efficiently linked to immunoglobulins by the method of Wilson, supra.

Fluorescent labeled antibodies can be prepared from standard fluorescent moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers are described by Stryer, Science. 162:526 (1968) and Brand, L. et al, "Fluorescent probes for structure," Annual Review of Biochemistry. 41:843–868 (1972). The antibodies can be labeled with fluorescent groups by conventional procedures such as those disclosed in U.S. Pat. Nos. 3,940,475, 4,289,747 and 4,376,110, for example.

One group of fluorescers having a number of the desirable properties described above are the xanthene dyes, which include the fluoresceins derived from 3,6-dihydroxy-9-phenylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available.

Another group of fluorescent compounds are the naphthylamines, having an amino group in the alpha or beta position. Included among the naphthylamino compounds are 1-dimethylaminonaphthyl-5-sulfonate, 1-anilino-8-naphthalene sulfonate and 2-p-toluidinyl-6-naphthalene sulfonate. Other dyes include 3-phenyl-7-isocyanatocoumarin; acridines such as 9-isothiocyanatoacridine and acridine orange; N-[p-(2-benzoxazolyl)phenyl]maleimide; benzoxadiozoles such as 4-chloro-7-nitrobenzo-2-oxa-1,3-diazole and 7-(p-methoxybenzylamino)-4-nitrobenzo-2-oxa-1,3-diazole; stilbenes such as 4-dimethylamino-4'-isothiocyanatostilbene and 4-dimethylanimo-4'-maleimidostilbene; N,N'-dioctadecycloxacarboxyamine-p-toluenesulfonate; pyrenes such as 8-hydroxy-1,3,6-pyrenetrisulfonic acid, 1-pyrenebutyric acid, merocyanine 540, rose bengal, 2,4-diphenyl-3(2H)-furanone, o-phthaldehyde, as well as other readily available fluorescing molecules. These dyes either have active functionalities or such functionalities can be readily introduced. Other suitable fluorescent compounds are phycobiliproteins such as phycoerythrin, and lanthalide reagents.

For example, antibodies can be labeled with fluorochromes by the procedures described by Goding, J. MONOCLONAL ANTIBODIES: PRINCIPLES AND PRACTICE. New York: Academic Press, pp 208–249 (1983). The concentration of fluorochrome is selected according to the table of Goding, p 229. For example, fluorescein isocyanate (1.0 mg/ml) or rhodamine isocyanate (10.0 mg/ml) in DMSO is prepared, and the desired volume (1–10% of total protein solution volume) is added to the protein solution dropwise, with stirring. The reaction proceeds for two hours, shielded from light. The product is purified by gel filtration on SEPHADEX G-25 gel in PBS containing 0.1% $NaN_3$ to separate the unreacted or hydrolyzed fluorochrome. The absorbance of the conjugate is measured at 280 nm and at its peak in the visible region (495 nm for fluoresceinated antibody and 550 nm for rhodaminated antibody). The fluorochrome to protein ratio is calculated according to the procedure of Goding, supra, p 224–225. Conjugates are stored at 4C protected from light until use. If the antibody solution concentration is less than 1 mg/ml, BSA is added to the solution to a final concentration of 1 mg/ml.

The antibodies of this invention can be covalently bonded to avidin or biotin in one embodiment of this invention. Suitable binding procedures involve cross-linking through a bifunctional cross-linking agent. Suitable bifunctional compounds are described by Peters, K. et al Ann.Rev.Biochim. 46:523 (1977). Alkyl imidates show a high degree of specificity among the functional groups presented to them by a protein. The reaction is specific for primary amino groups. Examples of suitable coupling reagents include amidoesters such as dimethylmalonimidate, azides such as the acyl azide of tartryl diazide which reacts readily with immuno groups to produce amide linkages. Aryl dihalides (e.g., 1,5-difluoro-2,4-dinitrobenzene, or 4,4'-difluoro-3,3'-dinitrophenyl sulfone, glutaraldehyde, 1-ethyl-3-(3-dimethylaminopropyl)-carbodiimide hydrochloride, dimaleinide, mixed anhydride, m-maleamidobenzoyl N-hydroxysucciinimide ester, and other known cross-linking agents.

The foregoing reagents provide essentially irreversible bonds. Bifunctional agents with functional groups such as disulfide or glycol may be used. These provide bonds which can be broken after the cross-linking reaction, if desired. Such reagents include dimethyl 3,3'-dithiobispropionimidate, succinimidyl propionimidate, N-(3-fluoro-4,6-dinitrophenyl)-cystamine, tartryl diazide, tartryl di(glycylazide) and tartryl di(epsilon-amino caproylazide).

In other instances, the bonds can be formed directly between the reagents themselves. For example, antibody can be bound to biotin through functional groups on the respective materials. As a specific example, biotin can be treated with periodate and reacted with antibody to give a Schiff base formation without inhibiting the biotin to avidin binding or blocking immunological activity of the antibody.

Known techniques using bifunctional cross-linking agents include the following: (a) a one-step glutaraldehyde linkage, Avrameas, S., Immunochemistry. 6:43 (1969); (b) two-step glutaraldehyde linkage, Avrameas, S., Immunochemistry. 8:1175 (1971); and (c) dimaleimide linkage, Kato, K. et al, Euro.J.Biochem. 62:285 (1966).

Antibodies can be labeled with metallic radionuclides according the procedure of Hnatowich, A et al. Journal of Applied Radiation. 35(6):554–557(1984) and Buckley, R et al. Federation of European Biochemical Societies. 166(1):202–204 (Jan. 1984). In this procedure the antibodies are conjugated with a chelating agent such as diethylenetriamine pentaacetic acid which is capable of forming a chelate with the metallic radionuclide. A suspension of 0.1 mg/ml of the bicyclic anhydride of DTPA (diethylenetriamine pentaacetic acid) is prepared in a dry solvent such as chloroform, ether or dry DMSO. An aliquot is removed to a clean, dry tube sufficient to provide a DTPA to immunoglobulin molar ratio of 1:1 and evaporated under nitrogen. A 10–20 microliter portion of the antibody solution used (10–20 mg/ml) in 0.05M bicarbonate buffer in saline, pH 7.0–7.5 is added to the dry DTPA, and the contents are agitated for 0.5–1.0 min. The coupled protein preparation is diluted to 0.2 ml with the same buffer solution and purified on a 5 cm gel filtration column with SEPHADEX G-50 gel, using a saline eluant. The coupling efficiency is determined before purification by the addition of "chelation-grade" $^{111}$In in 0.5M acetate buffer solution, pH 6.0. Thin layer chromatograpy is used to separate the DTPA coupled antibody for calculation of the coupling efficiency. The DTPA-coupled antibodies can be stored at 4C until needed for binding with metallic radionuclides such as $^{111}$In$^{+3}$, $^{212}$Bi$^{+3}$ and $^{68}$Ga$^{+3}$, for example.

The secondary binding reagent is applied to the polysilicon surface in an aqueous solution. The solution preferably contains suitable salts and buffers to preserve the reactants and facilitate the conjugation reaction. For example, the solution can contain BSA, phosphate buffer solution (PBS) and a mild surfactant such as a polyoxyethylene sorbitan ester. The rinse solutions described hereinabove can also be used.

For use with an enzyme label, a preferred solution comprises from 0.0001 to 0.005 mg/ml of the enzyme labeled secondary binding reagent in an aqueous phosphate buffered solution having a phosphate molarity of from 0.005 to 0.1 and a pH of from 6 to 8. A beneficial component in the solution is polyethylene glycol having a molecular weight of from 1000 to 8000 in concentrations of from 1 to 8 wt. %. A further important ingredient is a non-ionic surfactant in concentrations of from 0.01 to 0.5 wt. %. A preferred non-ionic surfactant is TRITON X-405.

The incubation times required for conjugation of secondary binding reagent and analyte bound to the polysilicon surface is temperature dependent. At temperatures of from 18° to 40° C., incubation times of from 15 to 120 minutes can be used. At preferred temperatures of from 20° to 26° C., incubation times of from 30 to 60 minutes can be used. Excessive incubation reduces the efficacy of the process, and the shortest incubation times which yield the desired accuracy are preferred.

The solid support is then rinsed to remove residual, unconjugated enzyme labeled secondary binding reagent. The rinse solutions described above are suitable.

The further steps are selected to convert the label into a physically detectable moiety. When using a fluorogenic enzyme, the third step of this process comprises contacting the polysilicon surface with a solution of a substrate which undergoes chemical reaction in the presence of the fluorogenic enzyme for a time sufficient for fluorescent compounds to be formed. Suitable substrates and enzymes they are converted by are known in the art and are described in U.S. Pat. No. 4,190,496.

The equipment and procedures for determining the physically detectable label are conventional and well known in the art and are not a part of the invention. For determining the level of fluorescence in a solution, suitable fluorometers are the fluorometers by Perkin-Elmer, American Instrument Company, and Turner Designs. The Allergenetics Fluorometer (3M Diagnostics, Inc. Mountain View, California) is preferred.

Competition binding assays using the polysilicon surface can use known amounts of either the primary binding reagent or the reagent analyte bound to the surface. In one embodiment of this invention, the polysilicon surface has a known concentration of primary binding reagent adhered thereto. A mixture of the sample containing the analyte and a known concentration of labeled analyte is applied to the insoluble support for a time sufficient to permit analyte conjugation with the primary binding reagent to occur. The times and temperatures described above for primary binding reagent conjugation with analyte are suitable. After removing and rinsing the residual sample solution from the polysilicon surface, the label remaining on the polysilicon surface can be determined. If the label is a fluorogenic enzyme, the amount of label on the polysilicon surface can be determined by contacting the surface with a suitable substrate solution, permitting the reaction yielding the fluorophore in the solution, and measuring the fluorescence level, as described above with respect to the sandwich binding assay embodiment.

In another embodiment of a competition binding assay, the polysilicon surface has a known quantity of reagent analyte adhered thereto. A mixture of the sample solution and and a known amount of primary binding reagent which selectively binds with the analyte is then incubated with the polysilicon surface for a time sufficient to permit analyte conjugation with primary binding reagent. The amount of label on the polysilicon surface is then determined. If the label is a fluorogenic enzyme, the amount of label on the polysilicon surface can be determined by contacting the surface with a suitable substrate solution, permitting the reaction yielding the fluorophore in the solution, and measuring the fluorescence level, as described above with respect to the sandwich binding assay embodiment.

The use of a polysilicon surface as the insoluble support for the binding reagents makes available a reagent with greatly reduced non-specific binding. With the polysilicon surface, the non-specific binding can be reduced to a near zero value with appropriate non-specific binding inhibitors, a major improvement over other insoluble supports.

This invention is further illustrated by the following specific, but non-limiting examples. Temperatures are given in degrees Centigrade and percents as weight percents unless otherwise specified. Examples which are constructively reduced to practice herein are presented in the present tense, and examples representing laboratory experiments previously reduced to practice are presented in the past tense.

EXAMPLE 1

Polysilicon with Anti-Streptococcus Antibody

To a glass petri disk with polysilicon chips in the bottom thereof is added a solution of rabbit anti-(Streptococcus A) antibody. The antibody is applied is a solution of 0.01M phosphate buffered solution, pH 7.4, with 0.1 wt. % sodium azide preservative. The coating process is allowed to proceed at rm temp for 2 hrs (or overnight). At the end of the coating process, the liquid in the petri dish is removed by aspiration, and the polysilicon chips are air-dried at rm temp for 1 hr.

The chips are then contacted with a 0.01M phosphate buffer solution (PBS), pH 7.4, containing 2.5 wt. % sucrose, 0.25 wt. % bovine serum albumin, and 0.05 wt. % sodium azide, the excess is removed, and the chip is vacuum dried and stored in a sealed container. The chip can be used for assaying patient serum for Strep. A.

EXAMPLE 2

Polysilicon with Anti-theophylline Antibody

Repeating the procedure of Example 1 but replacing the rabbit anti-(Streptococcus A) antibody with rabbit anti-theophylline antibody yields chips of polysilicon coated with the anti-theophylline antibody.

EXAMPLE 3

Streptococcus A Immunoassay

A polysilicon chip product of Example 1 to which anti-(Streptococcus A) antibody is adhered, is contacted with patient throat swab extract containing Streptococcus A antigen and incubated for 1 hr. The sample solution is removed, and the chip washed 3 times with buffered rinse solution containing 0.85 wt. % sodium chloride, and 0.1 wt. % sodium azide preservative in a 0.01 aqueous phosphate buffer solution, pH 7.4. Patient sample Streptococcus A antigen is conjugated to the polysilicon surface.

The polysilicon chip is then contacted for 30 min with 600 microliters of a solution of rabbit anti-(Streptococcus A) antibody conjugated to horse radish peroxidase. The antibody-enzyme conjugate is applied in a solution of 0.01M phosphate buffered saline, pH 7.4, containing 4 wt. % polyethylene glycol having a molecular weight of 4000 (PEG 4000), 0.5 wt. % BSA, and 0.1 wt. % sodium azide preservative. The horse radish peroxidase conjugated anti-(Streptococcus A) antibody solution is removed by aspiration, and the chip rinsed 3 times with the buffered rinse solution described above.

To the polysilicon chip in a 12×75 mm glass test tube is then added 600 microliters of a substrate solution containing $2 \times 10^{-3}$M 2,2'-azino-bis-(3-ethyl benzothiazoline-6-sulfonic acid)-diammonium salt, pH 4.5, in citrate buffer solution (0.05M) in deionized water containing 0.02 mM EDTA. After 20 min, the optical density at 342 nm is read with a spectrophotometer. By comparing the reading with levels measured by repeating the procedure with control solutions having known concentrations of Streptococcus A antigen, the total Streptococcus A antigen level in the patient sample is determined.

EXAMPLE 4

Theophylline Immunoassay

Repeating the procedure of Example 3 but replacing the polysilicon chip coated with anti-theophylline antibody prepared by the procedure of Example 3 and the sample with a patient serum sample, a reading which is a function of the theophylline level in the patient serum is obtained. By comparing the reading with levels measured by repeating the procedure with control solutions having known concentrations of theophylline, the theophylline level in the patient serum is determined.

We claim:

1. A polysilicon binding assay surface having a binding reagent adhered thereto and having a non-specific binding inhiitor adsorbed to the surface thereof.

2. The polysilicon binding assay surface of claim 1 wherein the binding reagent is selected from the group consisting of antibody, antigen, hapten, protein A, lectin, biotin, avidin and nucleotide sequence.

3. The polysilicon binding assay surface of claim 1 wherein the non-specific binding inhibitor is a water-soluble protein or polyamino acid.

4. A solid binding assay device having mounted on a surface thereof, a polysilicon binding assay surface of claim 1.

5. The solid binding assay device of claim 4 wherein the body of the device is made of a composition which does not introduce significant non-specific binding.

6. The solid binding assay device of claim 4 wherein the device is a dipstick.

7. A binding assay method comprising the steps of
   (a) contacting the polysilicon binding assay surface of claim 1 with a sample solution containing an analyte which is specifically bound by the binding reagent for a time sufficient to permit conjugation between the binding reagent and the analyte;
   (b) removing residual sample solution from the polysilicon surface; and
   (c) determining the analyte bound to the polysilicon surface.

8. The binding assay method of claim 7 wherein the non-specific binding inhibitor is a water-soluble non-immune protein or polyamino acid.

9. The binding assay method of claim 7 wherein the binding reagent is a primary binding reagent and the analyte bound to the polysilicon surface is determined in Step (c) by contacting the polysilicon surface with a reagent solution of a labeled secondary binding reagent which binds specifically with the analyte for a time sufficient for analyte conjugation with the secondary binding reagent to occur, removing residual reagent solution, and determining the label bound to the polysilicon surface.

10. The binding assay method of claim 9 wherein the label is an enzyme, chromophore, fluorophore, or radioactive compound.

11. The binding assay method of claim 10 wherein the label is an enzyme and the enzyme label is determined by contacting the insoluble support with a substrate which in the presence of the enzyme, produces a detectable chromophore or fluorophore, and determining the chromophore or fluorophore produced thereby.

12. The binding assay method of claim 11 wherein the enzyme is horseradish peroxidase, $\beta$-galactosidase or alkaline phosphatase.

13. The binding assay method of of claim 7 wherein the polysilicon surface is mounted on a solid binding assay device.

14. The binding assay method of claim 13 wherein the the body of the binding assay device is made of a non-specific binding composition.

15. The binding assay method of claim 13 wherein the device is a dipstick.

* * * * *